United States Patent [19]

DeOliveira et al.

[11] Patent Number: 4,872,454
[45] Date of Patent: Oct. 10, 1989

[54] FLUID CONTROL ELECTROSURGICAL DEVICE

[75] Inventors: Egidio L. DeOliveira, Fairport; John R. Scoville, Henrietta, both of N.Y.

[73] Assignee: Lucas DeOliveira, Fairport, N.Y.

[21] Appl. No.: 307,050

[22] Filed: Feb. 7, 1989

Related U.S. Application Data

[63] Continuation-in-part of Ser. No. 47,502, May 7, 1987, abandoned, which is a continuation of Ser. No. 787,685, Oct. 15, 1985, abandoned.

[51] Int. Cl.⁴ ............................................. A16B 17/36
[52] U.S. Cl. ........................... 128/303.14; 128/303.17
[58] Field of Search ...................... 128/303.13–303.17; 200/81 R, 81 H, 81.4, 81.5, 81.9 R

[56] References Cited

U.S. PATENT DOCUMENTS

| | | |
|---|---|---|
| 3,494,363 | 2/1970 | Jackson. |
| 3,828,780 | 8/1974 | Morrison ........................ 128/303.17 |
| 3,974,833 | 8/1976 | Durden ........................... 128/303.17 |
| 4,118,612 | 10/1978 | Gabus .................................. 200/81.9 |
| 4,545,375 | 10/1985 | Cline ............................... 128/303.14 |

*Primary Examiner*—Max Hindenburg
*Attorney, Agent, or Firm*—Marjama & Pincelli

[57] ABSTRACT

A control device for use with an electrical appliance. The device comprises a handpiece having at least one exhaust port which is connected to positive fluid pressure source. Blocking of the exhaust port will operate an appropriate switch means for controlling the electrical appliance.

10 Claims, 3 Drawing Sheets

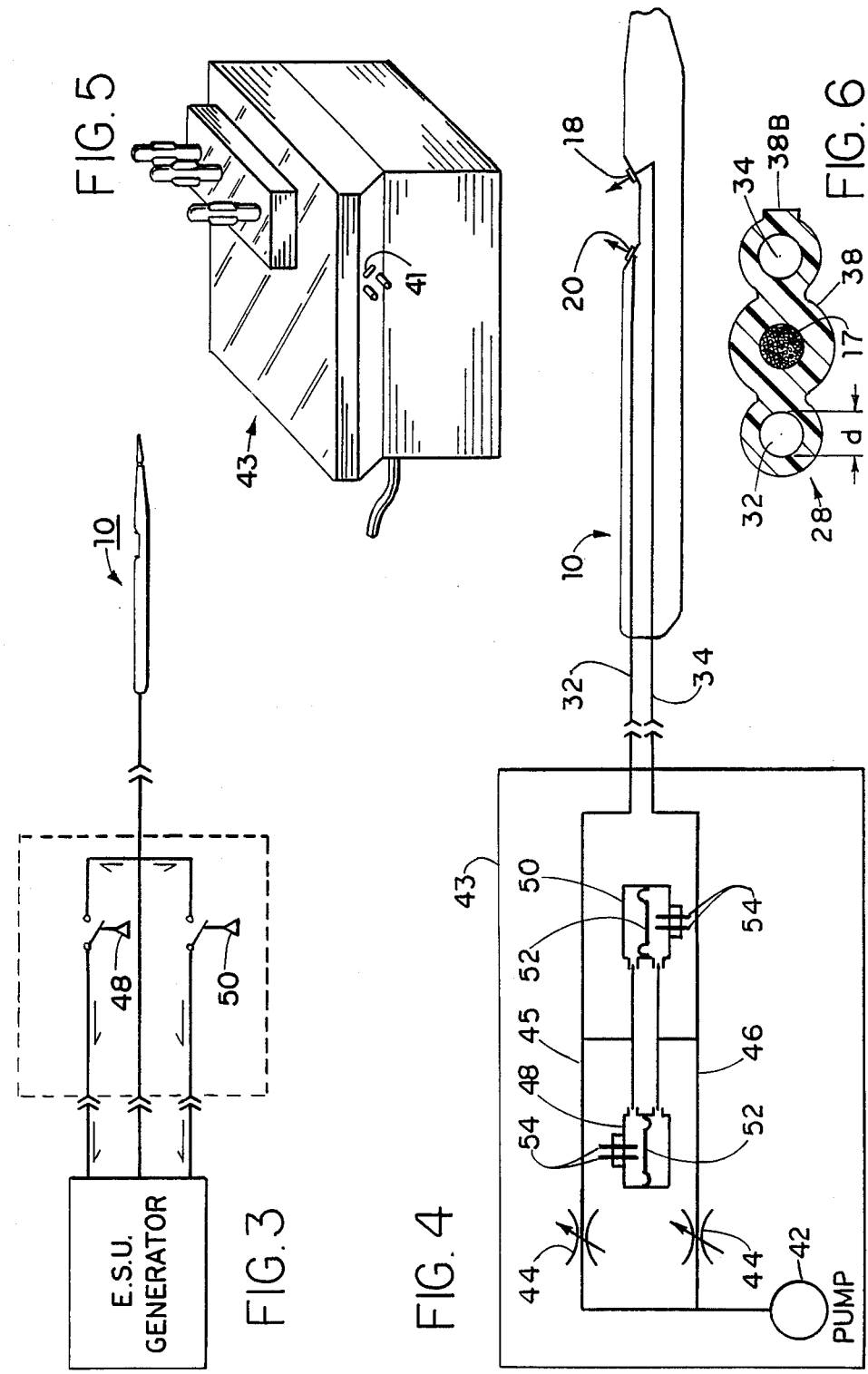

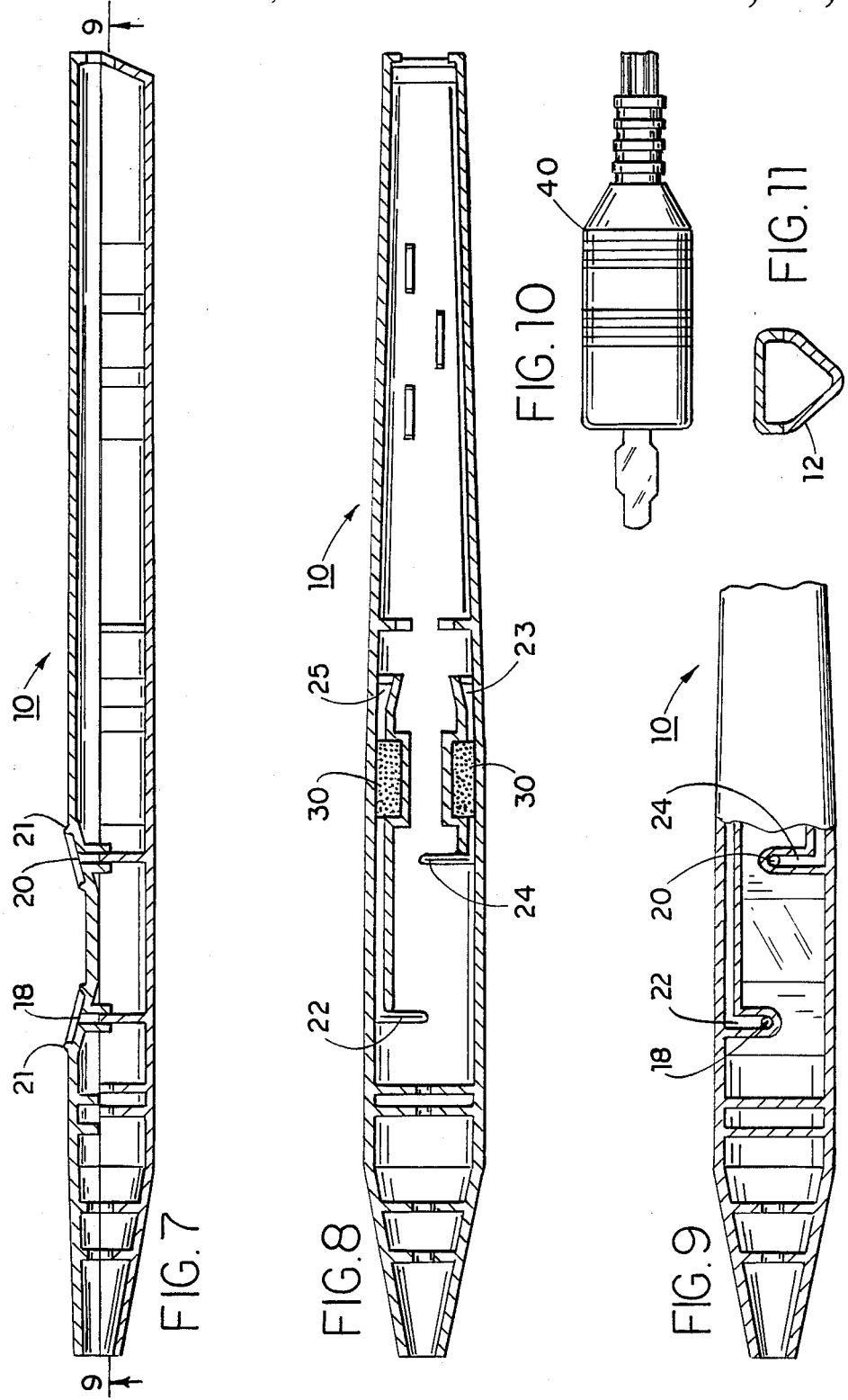

FLUID CONTROL ELECTROSURGICAL DEVICE

RELATED APPLICATIONS

This application is a continuation-in-part of application Ser. No. 07/047,502, filed May 7, 1987, now abandoned, which is a continuation of application Ser. No. 06/787,685, filed Oct. 15, 1985, now abandoned.

BACKGROUND OF THE INVENTION

The present invention is directed to a method and apparatus for controlling the electrical status of an electrosurgical generator and, in particular to a handpiece and method for controlling the output of an electrosurgical generator.

Electrosurgical generators are generally controlled by a handpiece used by the physcian. These handpieces are generally designed for single use and are then discarded. Handpieces of the prior art have mechanical switches incorporated within the device to control the status of the electrosurgical generator. By positioning the switch in the appropriate position, the electrosurgical generator may be used either for coagulation or cutting as desired by the physician. These switches comprise several components which require some type of force to be exerted on them by the operator in order to actuate the device.

U.S. Pat. No. 3,494,363 discloses controlling an electrosurgical generator by the use of a vacuum line or a confined volume of fluid by using some type of squeeze bulb to operate and modulate the pressure to control the desired status of the electrosurgical generator. The use of a vacuum has the inherent disadvantage in that the tube can become clogged by debris or other liquids. Further, debris or contaminants that have been collected by the vacuum device must be disposed of. The control squeeze bulb disclosed in the 3,494,363 patent requires a learned skill in order to obtain the desired electrical status of the electrosurgical generator. Use of a squeeze bulb for single use is relatively expensive. Additionally, repeated use of the squeeze bulb would most likely require resterilization.

SUMMARY OF THE INVENTION

A control device for use with an electrosurgical generator comprising a handpiece having at least one exhaust port. A fluidic level pressure source provides a continuous flow of a fluid. A transmission tube connects the fluidic pressure source to the exhaust port of the handpiece. Blocking the exhaust port activates a remote switch which controls the electrical status of the electrosurgical generator. The electrosurgical control device and method of the present invention is inexpensive to produce and operate yet provides reliable operation, contains no moving parts and requires no special skill to use.

DESCRIPTION OF THE DRAWINGS

FIG. 3 is an electrical schematic diagram of the control device made in accordance with the present invention;

FIG. 4 is a schematic diagram of the fluid piping for the control device of the present invention;

FIG. 5 is a perspective view of an adapter package of the control device of the present invention;

FIG. 6 is a cross-sectional view of the cable connected to the handpiece shown in FIG. 1;

FIG. 7 is a cross-sectional view of the handpiece of FIG. 1 taken along line 7—7;

FIG. 8 is a cross-sectional view similar to FIG. 2 illustrating the entire body of the handpiece of the present invention;

FIG. 9 is a partial cross-sectional view of the handpiece made in accordance with the present invention taken along line 9—9 of FIG. 7; and FIG. 10 is a side view of the plug end of the cable of the control device which connects to the adapter package and FIG. 5.

FIG. 11 is a cross-sectional view of the handpiece taken along line 11—11 of FIG. 1.

DETAILED DESCRIPTION OF THE PRESENT INVENTION

Figure 1:
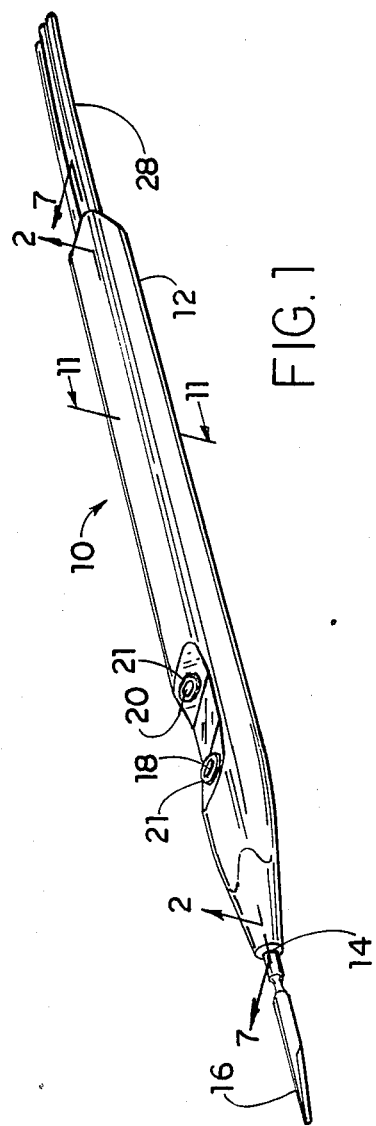
FIG. 1 is a perspective view of a handpiece for use in the control device of the present invention.
Figure 2:
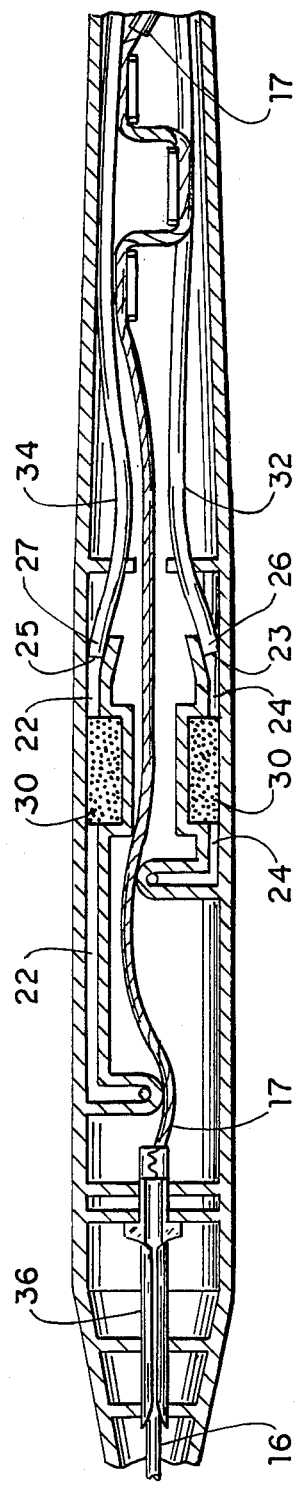
FIG. 2 is a partial cross-sectional view of the handpiece of FIG. 1 taken along line 2—2.

Referring to FIGS. 1 and 2, there is illustrated a handpiece 10 made in accordance with the present invention. Handpiece 10 is formed of a molded polystyrene plastic body 12 having an opening 14 at one end for receiving a blade 16. Removable blade 16 makes electrical contact with receptacle 36 which is electrically connected through wire 17 to the output of an electrosurgical generator, not shown. Body 10 is provided with a pair of openings or exhaust ports 18 and 20 which are connected by passageways 22 and 24 respectively to input ports 25 and 23. A cable 28 with transmission tubes 32 and 34 connects to input ports 23 and 25 to a fluidic level pressure source. Terminal ends 26 and 27 of transmission tubes 32 and 34, respectively, are each connected to input ports 23 and 25, respectively in any appropriate manner so as to provide a substantially sealed pathway for flow of a pressurized fluid. In the particular embodiment illustrated ends 26 and 27 are frictionally connected to input ports 23 and 25. Filters 30 are located between input ports 23 and 25 and output ports 18 and 20 respectively.

In the particular preferred embodiment illustrated in FIG. 11 is an unique modified triangular cross-section shape provided to eliminate torsional movement and correct alignment and position of the electrosurgical instrument and its said two exhaust ports, while within the grasp of the surgeon's hand.

Referring to FIGS. 7 and 1, there is illustrated a preferred configuration wherein two exhaust ports 18 and 20 are located on two opposing inclined surfaces separated continuously by, but connected to, a lower horizontal surface. This preferred configuration provides the benefit of allowing the surgeon to transfer from one mode to the other without having to lift his finger, and also protecting said two exhaust ports from inadvertent blockage, hence the unintended activation of the cut or coagulation modes. A raised ridge 21 may be located around each said two exhaust ports 18 and 20 to assist in sealing said exhaust ports. Ridge 21 is generally elliptical or circular in shape as illustrated in FIG. 1.

Referring to FIGS. 2 and 6, a cross-sectional view of cable 28 is illustrated. The cable is provided with two transmission tubes 32 and 34 respectively for connection with passageways 24 and 22. An electrically conductive wire 17 is, as previously stated, connected to blade 16 by receptacle 36. The outer cover 38 of the cable is formed of a non-conductive material which has flexible characteristics to allow flexing of the cable 28 yet is of sufficient rigidity to prevent kinking of the cable so that transmission tubes 32 and 34 will not collapse or become blocked or allow wire 17 to fracture or become severed. In the preferred embodiment, the two transmission tubes 32 and 34 are located on opposite sides of the conductive wire 17 so as to provide a generally flat configuration. The wire 17 in this flat configuration provides desired rigidity to prevent inadvertent collapse of the transmission tubes when pinched. This flat configuration provides the added benefit of reduced torsional force imparted on to the electrosurgical instrument as is characteristic of conventional round cross-sectional wire cable.

A rib 38B or other distinguishing feature such as stripe or notch is provided on the outside edge of one of the transmission tubes for the purpose of consistently identifying and locating the same transmission tube to the same exhaust port. This is important so that during manufacturing the port associated with the cut mode, for example, is always connected to the same transmission tube, hence eliminating cross-connection or reversed operating modes.

In the particular embodiment illustrated, the diameter d of transmission tubes 32 and 34 is about 0.030 inches (0.762 mm) and the overall length of cable 28 is approximately ten (10) feet (3.048 m). The other terminal end 40 (see FIG. 10) of the cable 28 is plugged into receptacle 41 of an adapter 43 (see FIG. 5) which provides the appropriate fluidic pressure source and electrical connection to the electrosurgical generator in response to controllng the exhaust ports 18 and 20.

FIG. 4 illustrates a schematic of the fluid piping of the present invention. In the particular embodiment illustrated, transmission tubes 32 and 34 are connected to a air pump 42 housed in adapter package 43. Air pump 42 is connected to two screw restrictors 44 to adjust the pressure in each parallel line 45 and 46 respectively to the desired level. In the present embodiment, the pressure level is the same due to the construction of the switches 48 and 50. Switches 48 and 50 operate in response to the closure or blockage of exhaust ports 18 and 20 respectively. Each switch has a membrane 52 having a conductive surface which will be displaced either to or away from electrodes 54 in response to a pressure being exerted against membrane 52. Exhaust ports 18 and 20 are fluidly connected to opposite sides of the membrane 52 for switches 48 and 50. When exhaust port 18 is blocked, for example by placing a finger over the exhaust port, a back pressure will be produced such that the membrane 52 of switch 50 will be moved away from electrodes 54 and membrane 52 of switch 48 will be moved toward electrode 54. Accordingly, the switch 48 will make contact thereby signaling operation of the electrosurgical generator in the appropriate mode, for example, coagulation. Whereas when exhaust port 20 is blocked membrane 52 of switch 50 will be forced against electrodes 54 and the membrane 52 of switch 48 will be displaced away from electrodes 54 thereby activating that part of the electrosurgical unit which controls cut mode. The switch 50 controls the cutting mode of the electrosurgical unit, therefore only one mode of electrosurgical unit will be activated by blocking either exhaust port 18 or 20. If both exhaust ports 18 and 20 are blocked by the operator, then neither of the switches 48 or 50 will be activated since substantially no differential pressure exists to activate the switches.

Referring to FIG. 3 there is illustrated an electrical schematic of the present invention. It can be seen that depending on whether switch 48 or 50 is in the closed position that this will determine whether the electrosurgical generator is in the cut or coagulate mode.

The pump 42 of the present invention is constructed such that the flow of the air is very low. While it is evident that the size of the passageways 22, 24, 32, and 34, and rate of flow of the fluid have an important affect on the flow of fluid through exhaust ports 18 and 20, the system is preferably designed such that the flow of fluid at exhaust ports 18 and 20 be very low such that it will not significantly disturb the air space adjacent the surgical site. Applicants have found that adequate operation of the system may be provided when the air flow is in the range of about 10 to 35 milliliters per minute. The line pressure, when measured at either ports of switches 48 and 50, respectively, for the particular size structure of the preferred embodiment, on both sides of the switches 48 and 50, is generally no greater than about 42 inches (106.68 cm) of water, preferably no greater than 30 inches (76.2 cm) of water and in the particular embodiment illustrated is in the range of about 15 to 17 inches (38.1 cm to 43.18 cm) of water. In the particular embodiment this is accomplished by the use of an aquarium pump by Whalinger Brothers "Whisper 100" model. However, any regulated pressure source that provides a continuous flow of fluid may be used, for example, air or gas pressure supply lines that are commonly available in operating rooms may be used or any pressurized bottled gas may be used. In such case a pressure regulator may be necessary to bring the supply pressure to the levels described.

The restrictors 44 as illustrated are made by Air Logics number F-2822-20. Here again, while restrictors 44 are not essential to the present invention, applicants have found them helpful in assuring the desired pressure level in both lines 45 and 46. The switches 48 and 50 of the present invention are switches produced by Clippard Corporation identified as Clippard Minmatic number 50100-3-NO. The filter 30 of the present invention is preferably of the type which will restrict any object or microorganism from passing therethrough, preferably common airborne particulates.

Applicants have found the actual size of exhaust ports 18 and 20 are not critical. It is more important that the trapped volume between the exhaust ports and switches be kept as low as possible so as to maintain appropriate response times. The system is designed such that the time delay between switching on or off of the electrosurgical generator is less than 200 milliseconds. In the particular embodiment illustrated, the time delay to turn on the electrosurgical generator is approximately 50 to 100 milliseconds and the time delay for turning the electrosurgical generator off is approximately 100 to 150 milliseconds.

While the present invention has been described as having two transmission tubes from the pressure source to exhaust ports 18 and 20 it is possible that only a single transmission tube may be used to control two different electrical modes of the electrosurgical generator. This can be achieved by incorporating a pressure transducer and associated electronic logic, instead of the pressure switch device at the adapter box and sensing the actuation mode by identifying the slope of the pressure versus time obtained by a combination of different size exhaust ports 18 and 20 with different length passageways within the handpiece.

As previously stated, larger capacity pumps or pressure sources can be used with the same arrangement or used with larger diameter passageways. The practice of the present invention is limited only to the use of a continuous gas supply to provide activating means to control the electrosurgical generator.

Another important aspect of the handpiece and apparatus of the present invention is that they are intrinsically safe from electrical shock. To confirm this claim, the device has been submerged in saline solution and tested according to current Association for the Advancement of Medical Instrumentation Standard for Electrosurgical Devices, AAMI HF18. As long as fluidic air flow is present the device may remain submerged indefinitely without the possibility of an electrical short circuit or unintended activation.

The present invention has also been described as controlling two different electrical modes of the electrosurgical unit, however, it may be desired to control an electrosurgical generator or other electrical appliances having only one mode. In such case only one exhaust port, passage and switch would be necessary.

Many variations may be made without departing from the scope of the present invention. For example, it may be possible to pipe the exhaust fluid to a remote location and some type of means may be used to block the passageway to provide the back pressure to cause the switches to activate. However, this does not benefit from the design simplicity of the preferred embodiment as it would require additional passageways and parts.

We claim:

1. A control device for use with an electrosurgical generator having two different electrical output modes comprising:
    (a) a handpiece having at least two exhaust ports;
    (b) a pressure source for providing a continuous flow of a fluid to each of said at least two exhaust ports;
    (c) a transmission tube having at least two passageways for connecting said pressure source to each of said at least two exhaust ports of said handpiece;
    (d) a fluid pressure responsive switch means connected by said passageways to said exhaust ports and a pressure source for activating one of said output modes in response to the blockage of at least one of said exhaust ports; and.
    (e) a blade at one end of said handpiece, said blade being electrically connected to the output of said electrosurgical generator.

2. A control device according to claim 1 wherein said fluid pressure responsive switch means comprises two switches each having a normally open position; said two switches being connected to said passageways such that when said two exhaust ports are unobstructed said two switches are in the normally open position and when one of said exhaust ports is blocked one of said two switches goes into the closed position so as to provide an electrical signal to activate one of said modes of said electrosurgical generator.

3. A control device according to claim 1 wherein when one of said exhaust ports is blocked a back pressure is provided at said fluid pressure switch means, said switch means being turned on or off in response to said back pressure.

4. An electrosurgical handpiece for controlling the status of an electrosurgical generator having two different electrical output modes comprising at least two exhaust ports for allowing passage of a fluid, at least one input port and a corresponding passageway connecting said input port to each of said exhaust ports, and a blade, said input port capable of being connected to a continuous flowing positive fluid pressure, said blade being electrically connected to the output of said electrosurgical generator.

5. An electrosurgical instrument which contains no moving parts and is capable of selectively providing electrical energy from an electrosurgical generator to a blade for cutting, coagulation and the like which comprises:
    (a) a body portion having at least one exhaust port, said body having a first end which contains an electrical receptacle, a second end and an intermediate portion therebetween;
    (b) a cable incorporating at least one open fluid transmission tube and one electrical contact wire within and extending throughout the length of said cable, and an electrical connector plug located at the distal end of said cable, incorporating a jack type electrical termination for said wire, and at least one passageway connecting the transmission tube to the face of the plug where the said jack is located;
    (c) means for connecting the distal end of said cable to a continuous flow of fluidic pressure level air supply and electrical energy switching source;
    (d) said proximal end of said cable being connected to said second end of said body portion so as to provide a substantially sealed pathway for the flow of fluidic pressure to said exhaust port;
    (e) a removable blade extending distally from said first end of said body portion and in electrical contact with said electrical receptacle, which is electrically connected to the output of an electrosurgical generator, said blade extending outwardly from said housing;
    (f) a remote source for providing a continuous flow of said fluidic air pressure; and
    (g) a remote switching means for controlling the electrical status of said electrosurgical generator.

6. An electrosurgical instrument according to claim 5 in which said instrument has two exhaust ports.

7. An electrosurgical instrument according to claim 6 in which said cable includes two transmission passageways for allowing transmission of said fluidic pressure from said pressure source, separately to each of said exhaust ports.

8. An electrosurgical instrument according to claim 6 in which said switching means are remote from said electrosurgical instrument and comprises two switches connected to said transmission tubes such that when said two exhaust ports are unobstructed said switches are in the normally open (quiescent) state and when one of the said exhaust ports is blocked, a corresponding switch goes into (or changes state) the closed position so as to provide the desired electrical energy wave form to said electrosurgical instrument.

9. An electrosurgery instrument according to claim 8 wherein the blockage of one said exhaust port causes the corresponding remote switch to go to the closed position and simultaneously forcing the other remote switch to remain in or transfer to the open position.

10. An electrosurgical instrument according to claim 6 in which said two exhaust ports are located on two opposing inclined surface thus preventing unintended blockage.

* * * * *